United States Patent [19]

Shioiri et al.

[11] 4,198,510
[45] Apr. 15, 1980

[54] PIPERIDENYLMETHYLIDENE PHOSPHONYLAMIDINES

[75] Inventors: Takayuki Shioiri, No. 18-14, 3-chome, Tsurumai, Showa-ku, Nagoya City, Aichi prefecture, Japan; Nobutaka Kawai, Tokyo; Masatoshi Ban, Gifu, both of Japan

[73] Assignees: Sanwa Kagaku Kenkyusho Co., Ltd., Nagoya; Takayuki Shioiri, Aichi, both of Japan

[21] Appl. No.: 922,524

[22] Filed: Jul. 7, 1978

[30] Foreign Application Priority Data

Oct. 17, 1977 [JP] Japan .................. 52-123594
Mar. 1, 1978 [JP] Japan .................. 53-023207
Mar. 1, 1978 [JP] Japan .................. 53-023208

[51] Int. Cl.$^2$ .............................................. C07F 9/24
[52] U.S. Cl. .................. 546/22; 260/326.5 C;
260/326.5 A; 260/326.5 CA; 260/326.5 M;
260/326.5 J; 260/570.5 R; 260/959; 544/157;
544/174; 544/178; 544/153; 546/196; 546/248;
546/184; 260/326.61; 260/326.87; 260/326.8;
260/346.71; 562/460; 562/465; 562/466;
562/490; 562/492; 562/496
[58] Field of Search .................................. 546/22

[56] References Cited

U.S. PATENT DOCUMENTS 3,949,022 4/1976 Hoffmann et al. ............. 546/22
3,975,522 8/1976 Bader ........................... 546/22

Primary Examiner—Alan L. Rotman
Assistant Examiner—Natalia Harkaway
Attorney, Agent, or Firm—Hammond & Littell, Weissenberger & Muserlian

[57] ABSTRACT

A process for the preparation of carboxylic acids represented by a formula

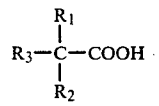

wherein $R_1$ represents hydrogen atom or a lower alkyl radical, $R_2$ represents hydrogen atom, lower alkyl or allyl radical and $R_3$ represents phenyl, substituted phenyl, substituted naphthyl, dibenzofuranyl or substituted biphenyl. Following novel enamine and amidine compounds as intermediates for manufacturing the carboxylic acids and processes for the manufacture of said enamine and amidine compounds

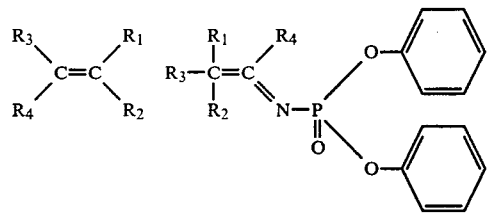

wherein $R_1$, $R_2$ and $R_3$ represent the meanings as referred to and $R_4$ represents dimethylamino, pyrrolidyl, piperidyl or morpholyl.

1 Claim, No Drawings

PIPERIDENYLMETHYLIDENE PHOSPHONYLAMIDINES

The present invention relates to a process for the preparation of carboxylic acids and intermediates therefor as well as the intermediates themselves and more particularly to novel enamine and amidine compounds and process for the preparation of the novel compounds as well as novel process for the preparation of known carboxylic acid derivatives through said novel compounds.

The final product of carboxylic acids are shown by the formula.

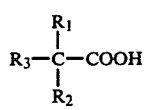
(I)

wherein $R_1$ represents hydrogen atom or lower alkyl radical, $R_2$ represents hydrogen atom, lower alkyl or allyl radical and $R_3$ represents phenyl, lower alkyl substituted phenyl, lower alkoxy substituted phenyl, cyclohexenyl substituted phenyl, benzoyl substituted phenyl, alkoxy substituted naphthyl, dibenzofuranyl, or halogen substituted biphenyl radical.

It has been well known that aromatic radical substituted carboxylic acids inclusive of the compounds (I) have antiphlogistic, analgesic, antifebrile actions and an action for preventing coagulation of blood (thrombus) and thus are usable as pharmaceutical agents (Jap. Pat. Publn. Nos. 7 491/1965, 22 297/1968, 18 105/1972 and others).

Hitherto, however, such aromatic radical substituted carboxylic acids have generally been prepared through 5 to 7 steps. This means it is not so preferable for the preparation thereof in industrial scale.

Therefore, a principal object of the present invention is to provide a novel process for the preparation of such carboxylic acids, which are reduced in number of process steps.

Another object of the present invention is to provide novel intermediates for preparing the carboxylic acids.

A still other object of the present invention is to provide a process for the preparation of such novel intermediates.

According to the present invention, the compounds (I) are prepared by subjecting a ketone represented by a formula $$R_3-CO-R_5 \quad (II)$$

wherein $R_3$ represents the meanings as referred to and $R_5$ represents a lower alkyl or vinyl ethyl radical, to react with a secondary amine represented by a formula $$R_4H \quad (III)$$

wherein $R_4$ represents dimethylamino, pyrrolidyl, piperidyl or morpholyl radical, in an inert solvent and in the presence of a dehydrating agent, subjecting the resulting enamine compound represented by a formula

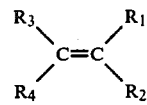
(IV)

wherein $R_1$, $R_2$, $R_3$ and $R_4$ represents the meanings as referred to, to react with Diphenyl Phosphorazidate (hereinafter referred merely to DPPA), and then hydrolyzing the resulting amidine compounds represented by a formula

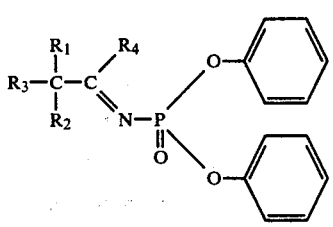
(V)

wherein $R_1$, $R_2$, $R_3$ and $R_4$ represent the meanings as referred to.

Almost all ketones as the raw material are commercially sold and easily available from markets but if necessary can be synthesized by utilizing Friedel-Crafts reaction [C. Friedel and J. M. Crafts "Compt. Rond" Vol. 84, pages 1392 and 1450 (1877)] or the like, as shown in the following formulae.

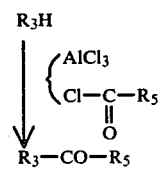

wherein $R_3$ and $R_5$ represent the meaning as referred to.

For synthesizing the enamine compounds (IV), benzene or toluene can be employed as the solvent and the amidine compounds (V) may be synthesized without isolating the corresponding enamine compounds. When it is desired that the enamine compounds would be isolated from the reaction mixture, ethyl acetate, tetrahydrofran, cyclohexane, N,N-dimethylformamide, N,N-dimethylsulfoxide or the like solvent may be employed in the synthesis of the amidine compounds, in addition to said solvents of benzene and toluene. It is preferable to use ethylene glycol as the solvent, when the amidine compounds are hydrolyzed.

The present invention will now be further explained with reference to Examples.

EXAMPLE 1

Preparation of 1-(1-phenyl-1-propenyl)-pyrrolidine

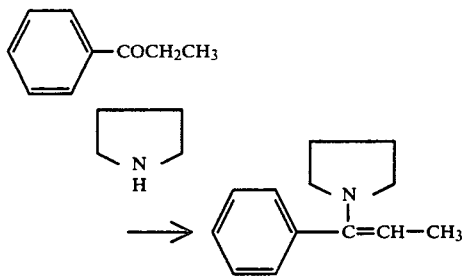

In 50 ml of benzene, 9.38 g of propiophenone, 14.93 g of pyrrolidine and 0.99 g of boron trifluoride etherate were dissolved. The mixture was refluxed for 67 hours using a Cope water separator and molecular sieve 4A as the dehydrating agent. After having distilled out the solvent under a reduced pressure, the residue was subjected to a distillation under a reduced pressure to obtain 10.33 g of the desired enamine (yield: 79%).

b.p. 101° C./3 mmHg.

EXAMPLE 2

Preparation of 1-(1-phenyl-1-butenyl) pyrrolidine

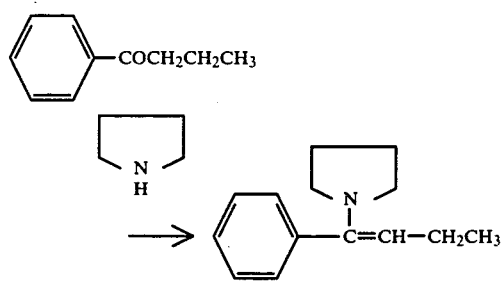

In 50 ml of toluene, 4.44 g of n-butyrophenone, 6.40 g of pyrrolidine and 0.43 g of boron trifluoride etherate were dissolved. The mixture was refluxed for 47 hours using a Cope water separator and molecular sieve 4A as the dehydrating agent. After having distilled out the solvent under a reduced pressure, the residue was subjected to a distillation under a reduced pressure to obtain the desired enamine as a pale yellowish oil (yield: 4.66 g, 77%).

b.p. 106° to 108° C./4 mmHg

NMR spectrum: δ ppm, CCl$_4$

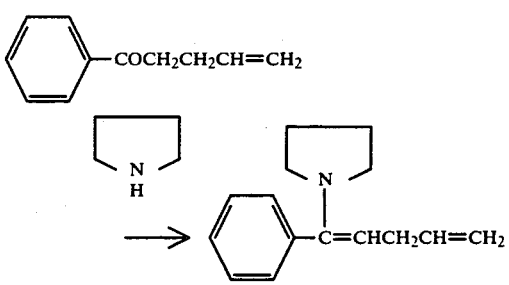

| a) 0.88 | (3H, t, J = 7.2Hz) |
| b) −1.78 | (6H, m) |
| c) 2.81 | (4H, m) |
| d) 4.23 | (1H, t, J = 7.2Hz) |
| e) 7.19 | (5H, s) |

EXAMPLE 3

Preparation of 1-(1-phenyl-1,4-pentadienyl) pyrrolidine

In 50 ml of toluene, 1.60 g of 4-pentenophenone, 2.13 g of pyrrolidine and 0.14 g of boron trifluoride etherate were dissolved. The mixture was refluxed for 46 hours using a Cope water separator and molecular sieve 4A as the dehydrating agent. After having distilled out the solvent under a reduced pressure, the residue was subjected to a distillation under a reduced pressure to obtain 1.68 g of the desired enamine (yield: 79%).

b.p. 80° to 84° C./0.15 mmHg

NMR spectrum: δ ppm, CCl$_4$

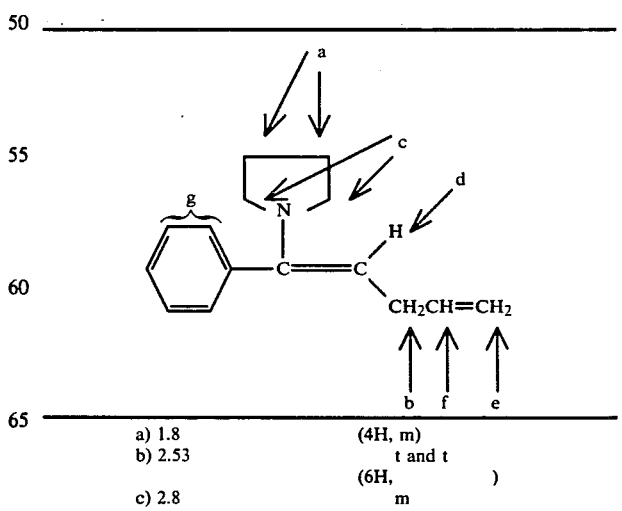

| a) 1.8 | (4H, m) |
| b) 2.53 | t and t |
|  | (6H, ) |
| c) 2.8 | m |

-continued

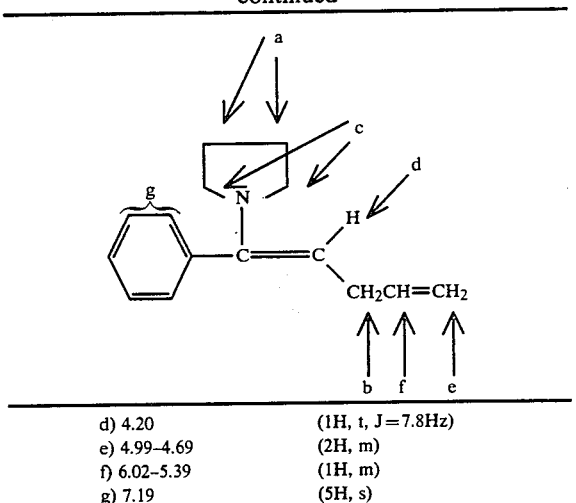

| d) 4.20 | (1H, t, J=7.8Hz) |
| e) 4.99–4.69 | (2H, m) |
| f) 6.02–5.39 | (1H, m) |
| g) 7.19 | (5H, s) |

EXAMPLE 4

Preparation of 1-(1-phenyl-1-propenyl) piperidine

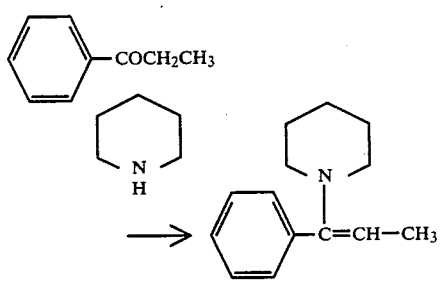

In 30 ml of toluene, 2.68 g of propiophenone, 5.30 g of piperidine and 0.14 g of boron trifluoride etherate were dissolved. The mixture was treated in a manner similar to Example 1 to obtain 2.50 g of the desired enamine (yield: 50%).

b.p. 99.5° to 100° C./3 mmHg

EXAMPLE 5

Preparation of 1-(1-phenyl-1-propenyl) morpholine

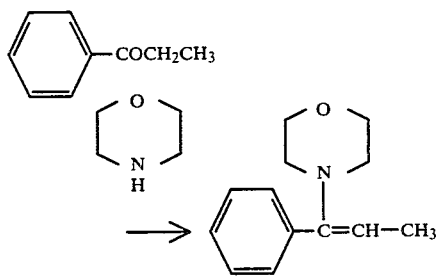

In 30 ml of toluene, 5.36 g of propiophenone, 0.45 g of morpholine and 0.28 g of boron trifluoride etherate were dissolved. The mixture was treated in a manner similar to Example 1 to obtain 4.46 g of the desired enamine (yield: 50.9%).

b.p. 103° C./3 mmHg

EXAMPLE 6

Preparation of 1-[1-(4-methoxyphenyl)-1-vinyl] pyrrolidine

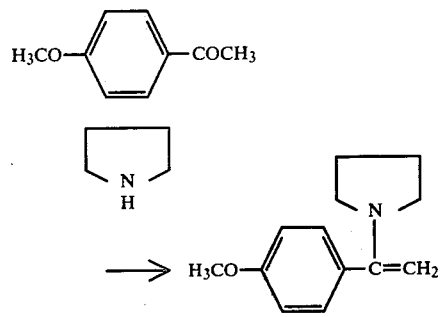

In 30 ml of toluene, 0.751 g of 4-methoxy acetophenone, 1.07 g of pyrrolidine and 0.03 g of boron trifluoride etherate were dissolved. The mixture was refluxed for 18 hours using a Cope water separator and molecular sieve 4A as the dehydrating agent. After having distilled out the solvent, the residue was subjected to a distillation under a reduced pressure to obtain 0.202 g of the desired enamine (yield: 20%).

NMR spectrum: δ ppm, $CCl_4$

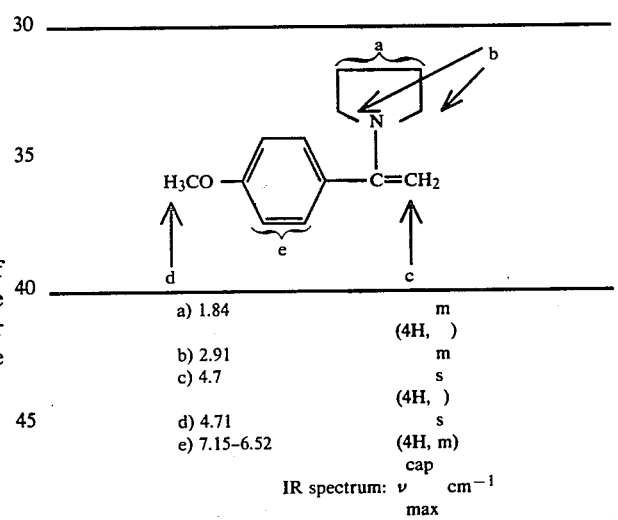

| a) 1.84 | m (4H, ) |
| b) 2.91 | m |
| c) 4.7 | s (4H, ) |
| d) 4.71 | s |
| e) 7.15–6.52 | (4H, m) |

IR spectrum: $\nu_{max}^{cap}$ $cm^{-1}$

IR spectrum: $\nu_{max}^{cap}$ $cm^{-1}$
1605, 1510, 1370, 1245, 1170, 1035 and 830

EXAMPLE 7

Preparation of 1-[1-(4-isobutylphenyl)-1-propenyl] pyrrolidine

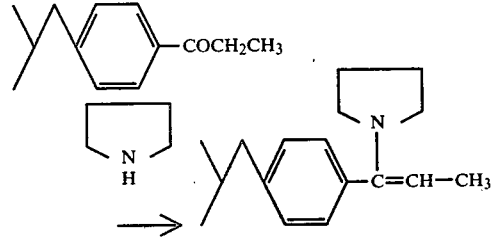

In 40 ml of dried benzene, 3.80 g of 4-isobutylpropiophenone, 4.27 g of pyrrolidine and 0.28 g of boron trifluoride etherate were dissolved. The mixture was refluxed for 50 hours using a Cope water separator and molecular sieve 4A as the dehydrating agent. After having distilled out the solvent under a reduced pressure, the residue was subjected to a distillation under a reduced pressure to obtain 3.84 g of the desired enamine (yield: 79%).

b.p. 112° to 114° C./0.4 mmHg

NMR spectrum: δ ppm, CCl₄

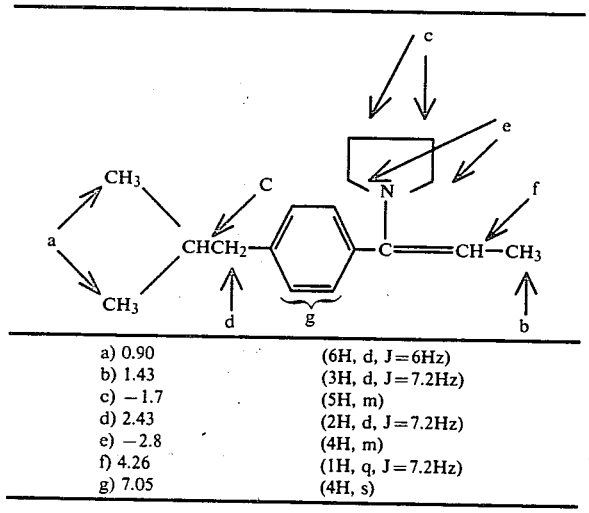

| a) 0.90 | (6H, d, J=6Hz) |
| b) 1.43 | (3H, d, J=7.2Hz) |
| c) −1.7 | (5H, m) |
| d) 2.43 | (2H, d, J=7.2Hz) |
| e) −2.8 | (4H, m) |
| f) 4.26 | (1H, q, J=7.2Hz) |
| g) 7.05 | (4H, s) |

The starting ketone was prepared in the following manner.

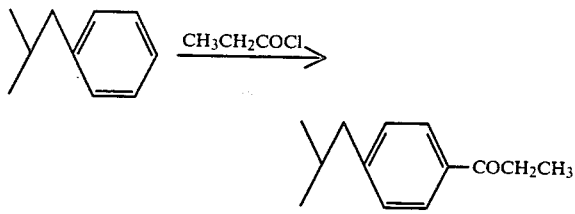

10.56 g of aluminum chloride was added in 36 ml of methylene chloride. To the resulting mixture, 7.77 g of propionylchloride was added drop-wise with stirring and ice cooling within 20 minutes. To the resulting mixture, 8.04 g of isobutylbenzene was added in drop-wise within 1 hour and then the mixture was stirred for 2 hours at room temperature and then kept to stand over night. The reaction mixture was poured into a mixture of 120 g of ice and 17 ml of conc. hydrochloric acid to obtain methylene chloride layer and then the water layer was extracted with chloroform. The both extracts were combined together, washed subsequently with water, 2% aqueous solution of sodium hydroxide and water, and dried on sodium sulfate. After having distilled out the solvent under a reduced pressure, the residue was subjected to a distillation under a reduced pressure to obtain the desired ketone (yield: 87%).

b.p. 86°-87° C./0.3 mmHg

The melting point of 2,4-dinitrophenylhydrazone of this compound was 170°–171.5° C.

Elemental Analysis: C₁₉H₂₂N₄O₄ Cal. C: 61.61; H: 5.99; N: 15.13; Found C: 61.72; H: 6.03; N: 14.85.

EXAMPLE 8

Preparation of 1-[1-(3-benzoylphenyl)-1-propenyl]pyrrolidine

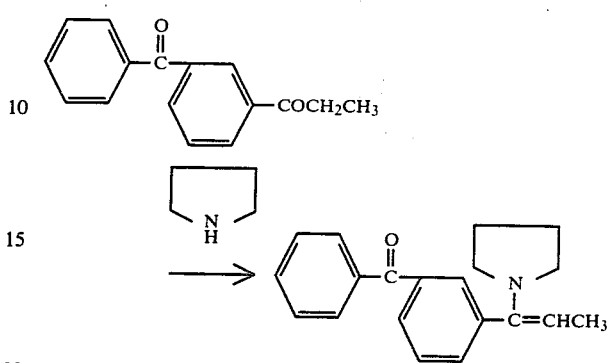

In 60 ml of toluene, 1.67 g of the starting ketone, 1.49 g of pyrrolidine and 0.10 g of boron trifluoride etherate were dissolved. The mixture was refluxed for 25 hours using a Cope water separator and molecular sieve 4A as the dehydrating agent. After having distilled out the solvent, the residue was subjected to a distillation under a reduced pressure to obtain 0.83 g of the desired enamine (yield: 41%).

b.p. 160° to 162° C./0.11 mmHg

NMR spectrum: δ ppm, CDCl₃

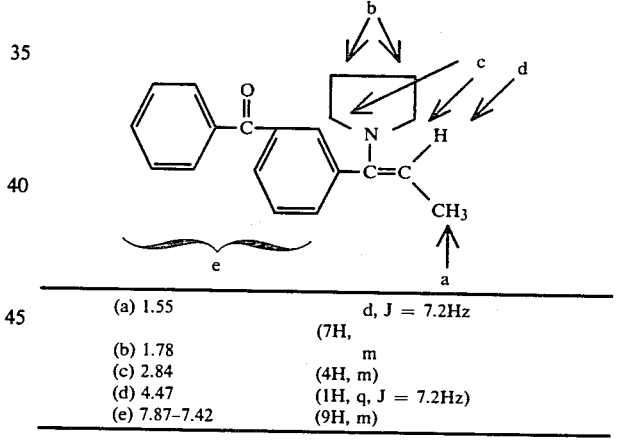

| (a) 1.55 | d, J = 7.2Hz (7H, |
| (b) 1.78 | m |
| (c) 2.84 | (4H, m) |
| (d) 4.47 | (1H, q, J = 7.2Hz) |
| (e) 7.87–7.42 | (9H, m) |

EXAMPLE 9

Preparation of 1-[1-(2-fluoro-4-biphenyl)-1-propenyl]pyrrolidine

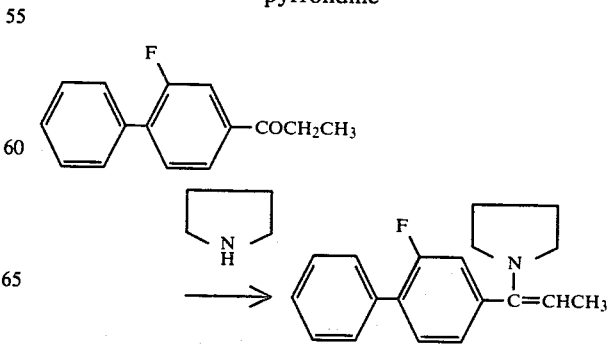

In 50 ml of toluene, 1.14 g of the starting ketone, 1.07 g of pyrrolidine and 0.07 g of boron trifluoride etherate were dissolved. The mixture was refluxed for 38 hours using a Cope water separator and molecular sieve 4A as the dehydrating agent. After having distilled out the solvent, a small amount of dried toluene was added to the residue and then ice-cooled. After having filtered to remove crystals, the filtrate was distilled to distill out the solvent under a reduced pressure and then the residue was subjected to a distillation under a reduced pressure to obtain 579 mg of the desired enamine (yield: 33%).

b.p. 136° to 138° C./3 mmHg
NMR spectrum: δ ppm, CDCl₃

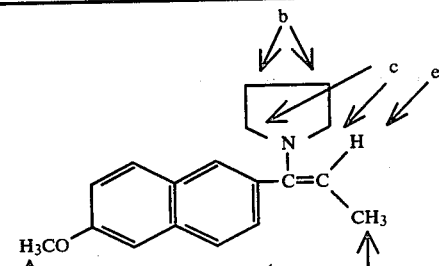

| (a) 1.54 | d, J = 6.6Hz |
| | (7H     m    ) |
| (b) 1.77 | |
| (c) 2.83 | (4H, m) |
| (d) 4.44 | (1H, q, J = 6.6Hz) |
| (e) 7.41–6.97 | (8H, m) |

EXAMPLE 10

Preparation of 1-[1-(6-methoxy-2-naphthyl)-1-propenyl] pyrrolidine

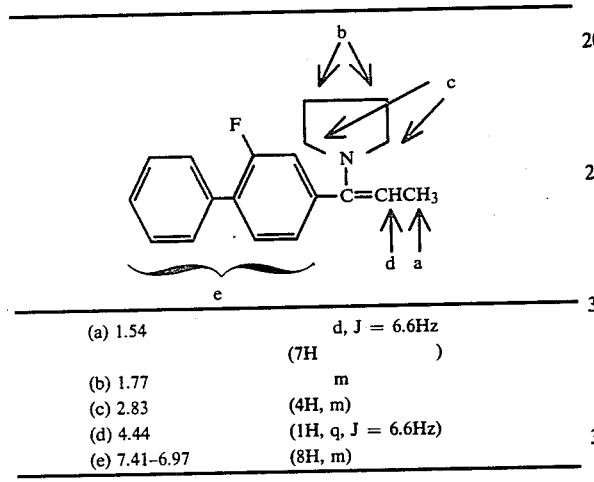

In 50 ml of benzene, 6.43 g of the starting ketone, 6.40 g of pyrrolidine and 0.43 g of boron trifluoride etherate were dissolved. The mixture was refluxed for 68 hours using a Cope water separator and molecular sieve 4A as the dehydrating agent. After having distilled out the solvent, the residue was subjected to a distillation under a reduced pressure to obtain 5.25 g of the desired enamine (yield: 65%).

b.p. 148° to 152° C./0.2 mmHg
NMR spectrum: δ ppm, CCl₄

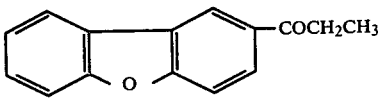

| (a) 1.52 | d, J = 7.2Hz |
| | (7H,     ) |
| (b) 1.79 | m |
| (c) 2.79 | (4H, m) |
| (d) 3.84 | (3H, s) |
| (e) 4.35 | (1H, q, J = 7.2Hz) |
| (f) 7.63–6.96 | (6H, m) |

EXAMPLE 11

Preparation of 1-[1-(2-dibenzofuranyl)-1-propenyl] pyrrolidine

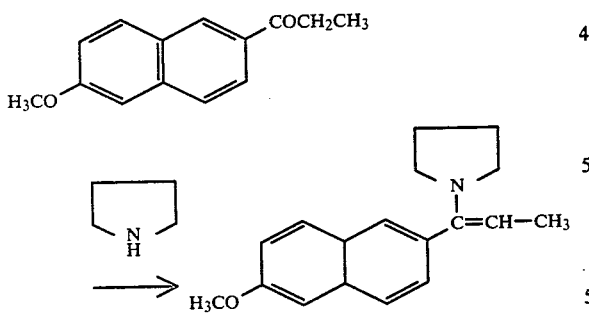

In 100 ml of toluene, 2 g of the starting ketone, 2.12 g of pyrrolidine and 0.14 g of boron trifluoride etherate were dissolved. The mixture was refluxed for 47 hours under argon atmosphere using a Cope water separator and molecular sieve 4A as the dehydrating agent. After having distilled out the solvent, the residue was subjected to a distillation under a reduced pressure to obtain 0.95 g of the desired enamine (yield: 34%).

b.p. 168° to 170° C./0.45 mmHg
NMR spectrum: δ ppm, CCl₄

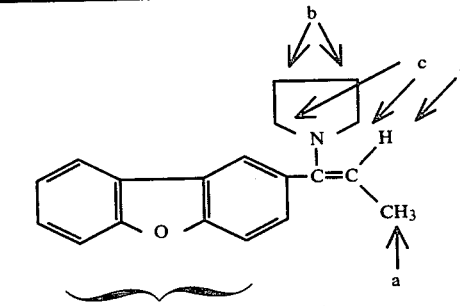

| (a) 1.51 | d, J = 7.2Hz |
| | (7H,     m     ) |
| (b) 1.75 | |
| (c) 2.83 | (4H, m) |
| (d) 4.37 | (1H, q, J = 7.2Hz) |

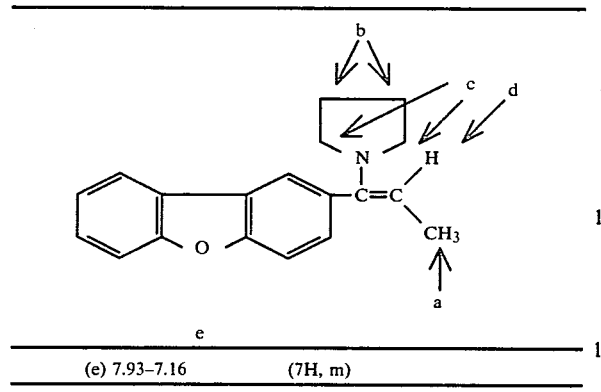

| e | |
|---|---|
| (e) 7.93–7.16 | (7H, m) |

EXAMPLE 12

Preparation of diphenyl N-(2-phenyl-1-pyrrolidinopropylidene) phosphoramidate

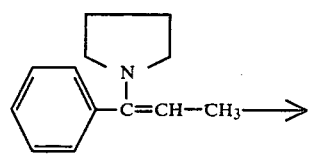

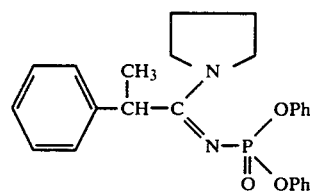

wherein Ph represents phenyl.

1.01 g of enamine prepared by the process as described in Example 1 was dissolved in 15 ml of ethyl acetate and to the resulting mixture, there was added in drop-wise 1.65 g of DPPA. The mixture was stirred for 1 hour at room temperature, heated at 40° C. to cause a reaction for 1 hour and then refluxed for 2 hours. To the resulting reaction solution, 100 ml of a mixture of ethyl acetate and benzene (1/1) was added and subsequently washed with each 30 ml of 5% citric acid solution, water, saturated sodium chloride solution, saturated sodium bicarbonate solution, water and saturated sodium chloride solution, dried on anhydrous magnesium sulfate and then distilled out the solvent under a reduced pressure. The residue was subjected to a silica-gel column chromatography with a mixture of benzene-ethyl acetate (1/5) to obtain 1.91 g of the crude phosphoryl amidine (yield: 81%). The crude compound was recrystallized from ethyl acetate-hexane to obtain colorless needles having melting point of 74° to 76° C.

Elemental Analysis ($C_{25}H_{27}N_2O_3P$):

Cal. C: 69.11; H: 6.26; N: 6.45; Found C: 68.72; H: 6.53; N: 6.47.

NMR spectrum: δ ppm, $CCl_4$

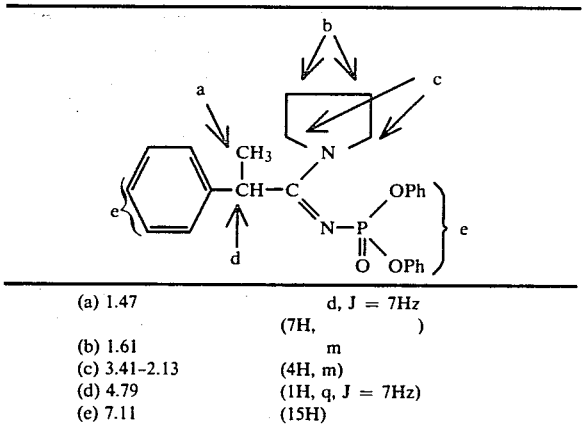

| (a) 1.47 | d, J = 7Hz |
|---|---|
| | (7H,    ) |
| (b) 1.61 | m |
| (c) 3.41–2.13 | (4H, m) |
| (d) 4.79 | (1H, q, J = 7Hz) |
| (e) 7.11 | (15H) |

EXAMPLE 13

A process similar to that as described in Example 12, excepting that tetrahydrofuran was employed in lieu of ethyl acetate, to obtain the desired compound at yield of 80%. Physical properties of the product were same with those of the compound obtained by the process as described in Example 12.

EXAMPLE 14

Preparation of diphenyl N-(2-phenyl-1-pyrrolidinopropylidene)phosphoramidate

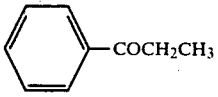

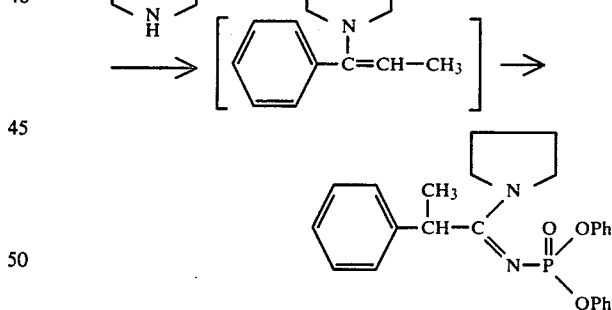

wherein Ph represents phenyl.

670 mg of propiophenone, 1.07 g of pyrrolidine and 0.07 g of boron trifluoride etherate were dissolved in 30 ml of toluene. The mixture was refluxed for 40 hours using a Cope water separator and molecular sieve 4A as the dehydrating agent. After having distilled out the solvent under a reduced pressure, 1.65 g of DPPA and 15 ml of tetrahydrofuran were added to the residue and the resulting mixture was stirred for 24 hours at room temperature and under argon atmosphere. Thereafter, the reaction mixture were subjected to the work up as described in Example 12 to obtain 1.83 g of the desired amidine (yield from ketone: 84%). Physical properties of the product were same with those of the compound obtained by the process as described in Example 12.

EXAMPLE 15

Preparation of diphenyl N-(2-phenyl-1-piperidinopropylidene)phosphoramidate

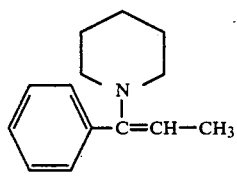

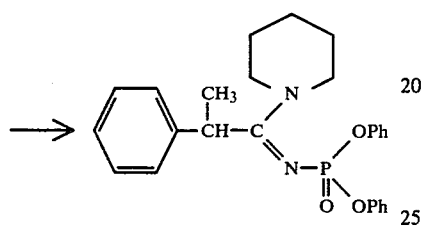

wherein Ph represents phenyl.

1.09 g of enamine prepared by the process as described in Example 4 and 1.65 g of DPPA were dissolved in 15 ml of ethyl acetate. The mixture was stirred for 75 minutes at room temperature, 30 minutes at 50° C. and 30 minutes at 80° C. and then refluxed for 3 hours. The reaction mixture was subjected to the work up as described in Example 12 to obtain 1.61 g of the desired amidine (yield: 67%).

The crude product was recrystalized from ethyl acetate-hexane to obtain colorless crystals having melting point of 67° to 69° C.

Elemental Analysis: $C_{26}H_{29}N_2O_3P$ Cal. C: 69.63; H: 6.52; N:6.25; Found C: 69.66; H: 6.60; N: 6.61.

NMR spectrum: δ ppm, CCl₄

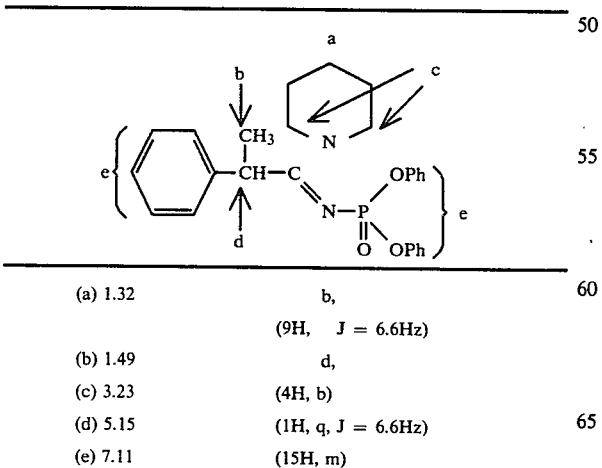

| | |
|---|---|
| (a) 1.32 | b, (9H, J = 6.6Hz) |
| (b) 1.49 | d, (4H, b) |
| (c) 3.23 | |
| (d) 5.15 | (1H, q, J = 6.6Hz) |
| (e) 7.11 | (15H, m) |

EXAMPLE 16

Preparation of diphenyl N-(2-phenyl-1-morpholinopropylidene)phosphoramidate

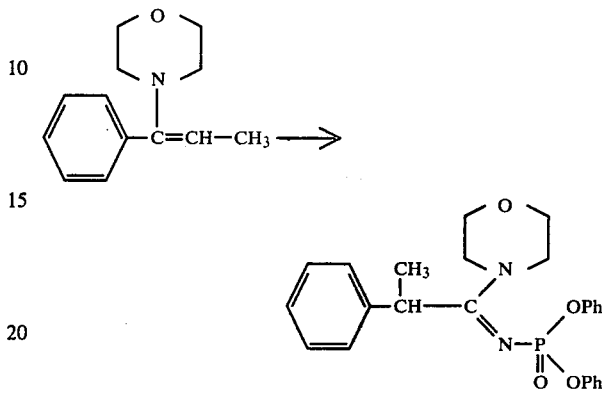

wherein Ph represents phenyl.

1.10 g of enamine as prepared by the process as described in Example 5 and 1.65 g of DPPA were dissolved in 15 ml of ethyl acetate. The mixture was stirred for 1 hour at room temperature and 15 minutes at 55° C. and then refluxed for 3 hours. The reaction mixture was subjected to the work up as described in Example 12 to obtain 1.54 g of the desired amidine (yield: 63%).

The crude product was recrystalized from ethyl acetate-hexane to obtain colorless prisms having melting point of 71° to 73.5° C.

Elemental Analysis: $C_{25}H_{27}N_2O_4P$ Cal. C: 66.65; H: 6.04; N: 6.22. Found C: 66.79; H: 6.12; N: 6.30.

NMR spectrum: δ ppm, CCl₄

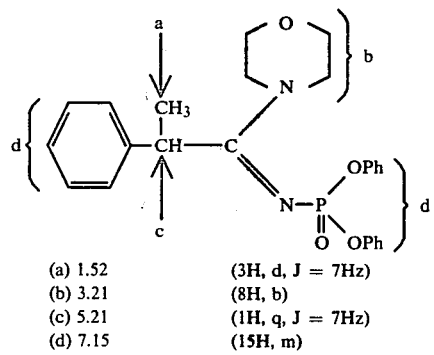

| | |
|---|---|
| (a) 1.52 | (3H, d, J = 7Hz) |
| (b) 3.21 | (8H, b) |
| (c) 5.21 | (1H, q, J = 7Hz) |
| (d) 7.15 | (15H, m) |

EXAMPLE 17

Preparation of diphenyl N-[2-(4-isobutylphenyl)-1-pyrrolidinopropylidine]phosphoramidate

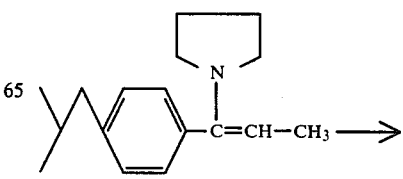

-continued

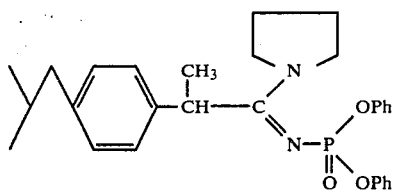

wherein Ph represents phenyl.

1.22 g of enamine prepared by the process as described in Example 7 and 1.65 g of DPPA were dissolved in 15 ml of tetrahydrofuran. The mixture was stirred for 1 hour at room temperature and 1 hour at 40° C. and then refluxed for 2 hours. The reaction mixture was subjected to the work up as described in Example 12 to obtain 1.87 g of the desired amidine as viscous oil (yield: 76%).

Elemental Analysis: $C_{29}H_{35}N_2O_3P$ Cal. C: 71.00; H: 7.19; N: 5.71; Found C: 71.01; H: 7.20; N: 5.76.

IR spectrum: $\nu_{max}^{cap}$ cm$^{-1}$
1565, 1493, 1246, 1222, 1203 and 920

NMR spectrum δ ppm, CCl$_4$

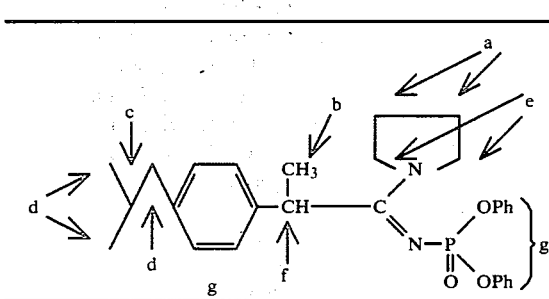

| (a) 0.90 | (6H, d, J = 6Hz) |
| (b) 1.43 | (3H, d, J = 7.2Hz) |
| (c) 1.7 | (5H, m) |
| (d) 2.43 | (2H, d, J = 7.2Hz) |
| (e) 2.8 | (4H, b) |
| (f) 4.26 | (1H, q, J = 7.2Hz) |
| (g) 7.05 | (4H, s) |

EXAMPLE 18

Preparation of diphenyl N-[2-(4-isobutylphenyl)-1-pyrrolidinopropylidene]-phosphoramidate

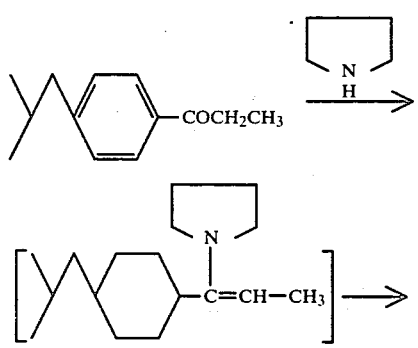

-continued

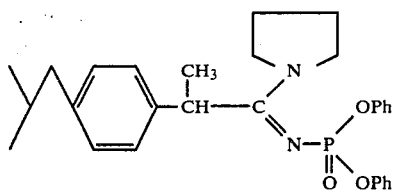

0.95 g of 4-isobutylpropiophenone prepared by the process as described in Example 7, 1.07 g of pyrrolidine and 0.07 g of boron trifluoride etherate were dissolved in 60 ml of benzene and reacted as described in Example 7. The reaction mixture was subjected to a distillation under a reduced pressure to remove the solvent and then 15 ml of tetrahydrofuran and 1.65 g of DPPA were added. The mixture was stirred for 1 hour at room temperature and 1 hour at 40° C. and then refluxed for 2 hours. The resulting reaction mixture was subjected to the work up as described in Example 12 to obtain 1.83 g of the desired amidine (yield: 75%).

Physical properties of the product were the same with those of the compound obtained by the process as described in Example 17.

EXAMPLE 19

A process similar to that as described in Example 18 excepting that the reaction was carried out under argon atmosphere was carried out to obtain 1.91 g of the desired amidine (yield: 78%). The product had physical properties as described in Example 17.

EXAMPLE 20

Preparation of diphenyl N-[2-(6-methoxy-2-naphthyl)-1-pyrrolidino-propylidene]phosphoramidate

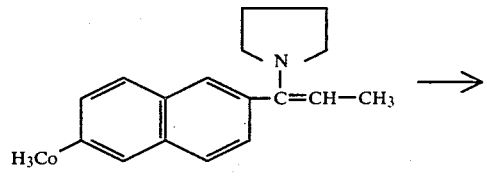

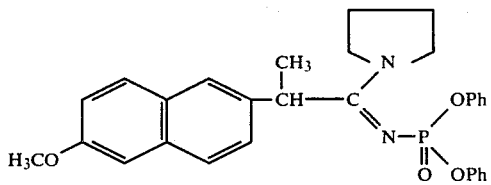

wherein Ph represents phenyl.

1.07 g of enamine prepared by the process as described in Example 10 and 1.32 g of DPPA were dissolved in 12 ml of tetrahydrofuran. The mixture was stirred under argon atmosphere for 1 hour at room temperature, 2 hours at 40° C. and 1 hour at 50° C. Thereafter, the resulting reaction mixture was subjected to the work up as described in Example 12 to obtain 1.33 g of the desired amidine (yield: 65%).

The crude product was recrystalized from ethyl acetate-hexane to obtain colorless needles having melting point of 102.5° to 105° C.

Elemental Analysis: $C_{30}H_{31}N_2O_3P$ Cal. C: 70.02; H: 6.07; N: 5.45; Found C: 70.18; H: 6.28; N: 5.52.

NMR spectrum: δ ppm, CDCl₃

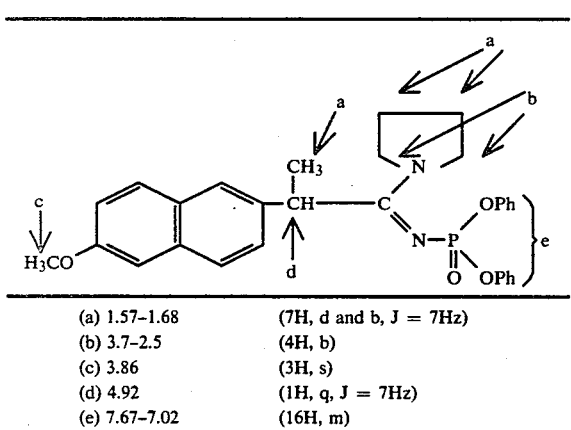

| (a) 1.57–1.68 | (7H, d and b, J = 7Hz) |
|---|---|
| (b) 3.7–2.5 | (4H, b) |
| (c) 3.86 | (3H, s) |
| (d) 4.92 | (1H, q, J = 7Hz) |
| (e) 7.67–7.02 | (16H, m) |

EXAMPLE 21

Preparation of diphenyl N-[2-(6-methoxy-2-naphthyl)-1-pyrrolidinopropylidene]phosphoramidate

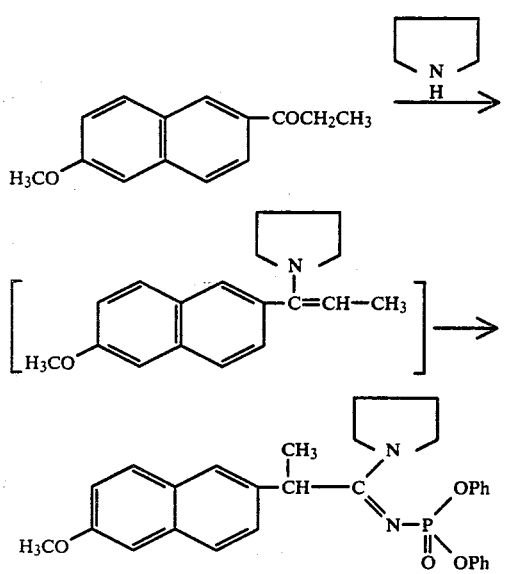

wherein Ph represents phenyl.

1.07 g of the starting ketone, 1.07 g of pyrrolidine and 0.07 g of boron trifluoride etherate were treated and reacted as described in Example 10. The reaction mixture was subjected to a distillation under a reduced pressure to remove the solvent and then under argon atmosphere, 15 ml of tetrahydrofuran and 1.65 g of DPPA were added. The mixture was stirred for 1 hour at room temperature and 1 hour at 40° C. and then refluxed for 2 hours. Thereafter, the resulting reaction mixture was subjected to the work up as described in Example 12 to obtain 2.10 g of the desired amidine (yield from the starting ketone: 82%).

Physical properties of the product were the same with those of the compound obtained by the process as described in Example 20.

EXAMPLE 22

Preparation of diphenyl N-(2-dibenzofuranyl-1-pyrrolidinopropylidene)phosphoramidate

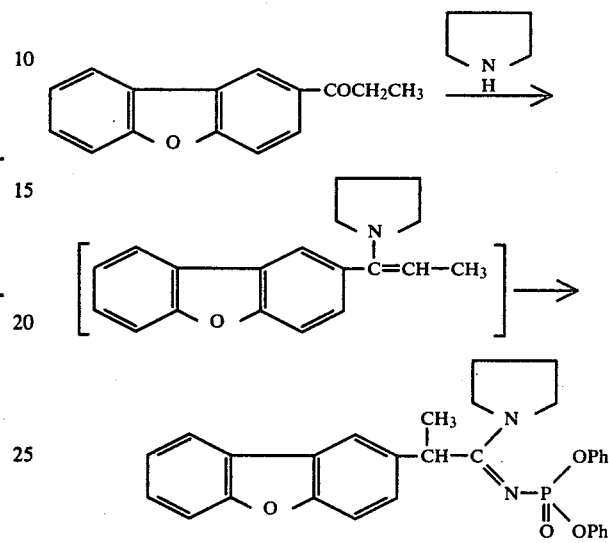

wherein Ph represents phenyl.

601 mg of the starting ketone, 640 mg of pyrrolidine and 40 mg of boron trifluoride etherate were dissolved in 30 ml of toluene. The mixture was refluxed for 42 hours under argon atmosphere and using a Cope water separator and molecular sieve 4A as the dehydrating agent. The reaction mixture was subjected to a distillation under a reduced pressure to remove the solvent and 9 ml of tetrahydrofuran and 990 mg of DPPA were added. The mixture was stirred under argon atmosphere for 1 hour at room temperature, 1 hour at 40° C. and then refluxed for 2 hours. The resulting reaction mixture was subjected to the work up as described in Example 12 to obtain 1.11 g of desired amidine (yield from the starting ketone: 71%).

IR spectrum: ν_{max}^{KBr} cm⁻¹
1560, 1482, 1241, 1218, 1195 and 916

NMR spectrum: δ ppm, CDCl₃

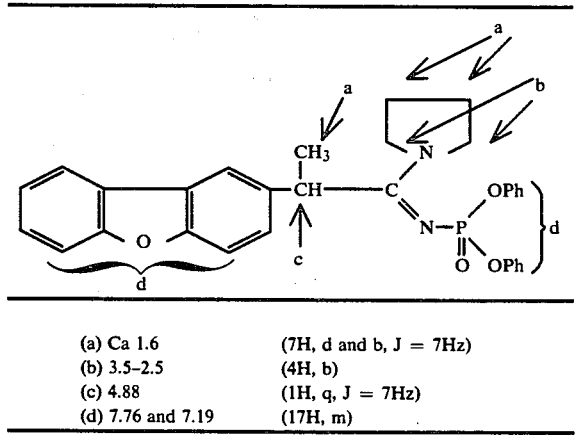

| (a) Ca 1.6 | (7H, d and b, J = 7Hz) |
|---|---|
| (b) 3.5–2.5 | (4H, b) |
| (c) 4.88 | (1H, q, J = 7Hz) |
| (d) 7.76 and 7.19 | (17H, m) |

EXAMPLE 23

Preparation of diphenyl N-[2-(3-benzoylphenyl)-1-pyrrolidinopropylidene]-phosphoramidate

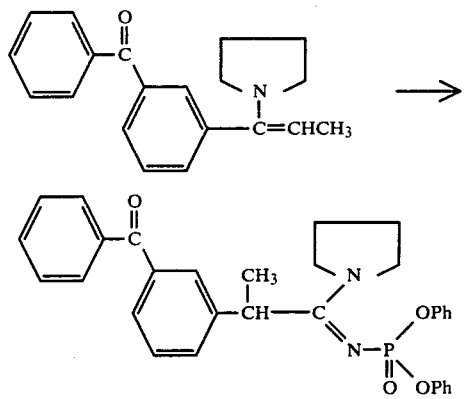

wherein Ph represents phenyl.

0.71 g of enamine prepared by the process as described in Example 8 and 0.81 g of DPPA were dissolved in 7.5 ml of tetrahydrofuran. The mixture was stirred under argon atmosphere for 1 hour at room temperature and 1 hour at 40° C. and then refluxed for 2 hours. To the reaction mixture, 60 ml of ethyl acetate-benzene (1:1 mixture) was added and washed subsequently with each 10 ml of 5% citric acid solution, water, saturated sodium chloride solution, saturated sodium bicarbonate solution, water and saturated sodium chloride solution, dried on anhydrous magnesium sulfate and then subjected to a distillation under a reduced pressure to remove the solvent. The residue was subjected to a silica-gel column chromatography with ethyl acetate-hexane (3:1 mixture) to obtain 0.93 g of the desired amidine (yield: 72%).

Elemental Analysis: $C_{32}H_{31}N_2O_4P$ Cal. C: 71.36; H: 5.80; N: 5.20; Found C: 71.66; H: 6.10; N: 5.07.

IR spectrum: $\nu_{max}^{KBr}$ cm$^{-1}$
1656 (C=O), 1559, 1484, 1241, 1196 and 918

NMR spectrum: δ ppm, CDCl$_3$

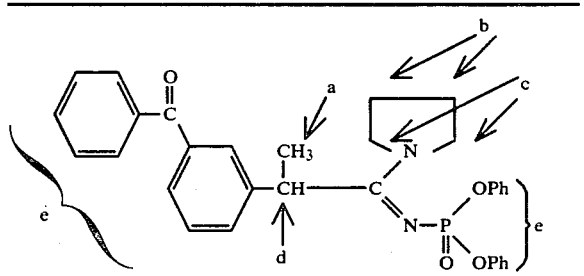

| (a) 1.54 | (7H, d, J = 7.2Hz) |
| (b) 1.63 | (7H, m, J = 7.2Hz) |
| (c) 3.4 and 3 | (4H, b) |
| (d) 4.82 | (1H, q, J = 7.2Hz) |
| (e) 7.75–7.15 | (19H, m) |

EXAMPLE 24

Preparation of diphenyl N-[2-(2-fluoro-4-biphenyl)-1-pyrrolidinopropylidene]-phosphoramidate

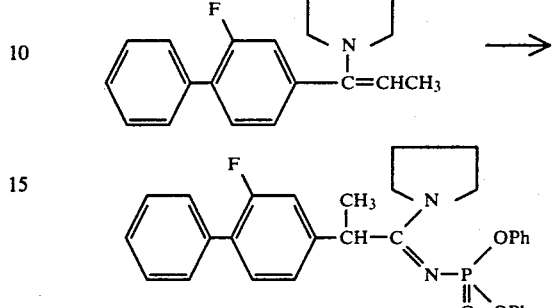

wherein Ph represents phenyl.

531 mg of enamine prepared by the process as described in Example 9 and 0.62 g of DPPA were dissolved in 6 ml of tetrahydrofuran. The mixture was stirred under argon atmosphere for 1 hour at room temperature and 1 hour at 40° C. and then refluxed for 2 hours. The reaction mixture was subjected to the work up as described in Example 12, excepting that the final reaction mixture was subjected to a silica-gel column chromatography with hexane-ethyl acetate (1:3 mixture), to obtain 674 mg of the desired amidine (yield: 68%). The crude product was recrystallized from ethyl acetate-hexane to obtain a colorless powder having melting point of 70°–73° C.

Elemental Analysis: $C_{31}H_{30}N_2O_3FP$ Cal. C: 70.44; H: 5.72; N: 5.30; Found C: 70.34; H: 5.95; N: 5.08.

NMR spectrum: δ ppm, CDCl$_3$

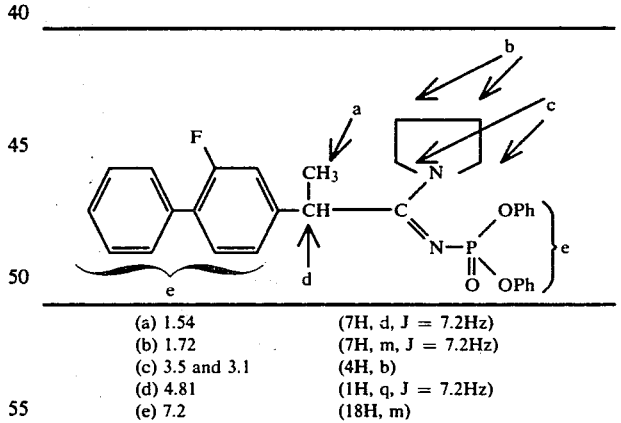

| (a) 1.54 | (7H, d, J = 7.2Hz) |
| (b) 1.72 | (7H, m, J = 7.2Hz) |
| (c) 3.5 and 3.1 | (4H, b) |
| (d) 4.81 | (1H, q, J = 7.2Hz) |
| (e) 7.2 | (18H, m) |

EXAMPLE 25

Preparation of diphenyl N-(2-phenyl-1-pyrrolidinobutylidene)phosphoramidate

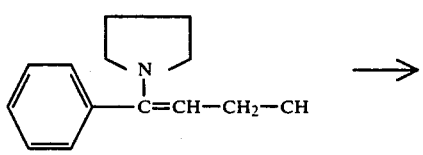

-continued

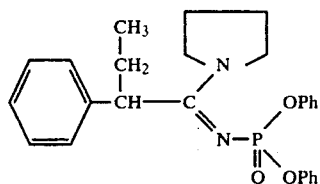

wherein Ph represents phenyl.

1.01 g of enamine prepared by the process as described in Example 2 and 1.65 g of DPPA were dissolved in 15 ml of tetrahydrofuran. The mixture was stirred for 1 hour at room temperature and 1 hour at 40° C. and then refluxed for 2 hours. The reaction mixture was subjected to the work up as described in Example 12 to obtain 1.67 g of the desired amidine (yield: 74%). The crude product was recrystallized from ethyl acetate-hexane to obtain colorless needles having melting point of 83° to 85° C.

Elemental Analysis: C₂₆H₂₉N₂O₃P Cal. C: 69.63; H: 6.52; N: 6.25; Found C: 69.80; H: 6.49; N: 6.25.

NMR spectrum: δ ppm, CCl₄

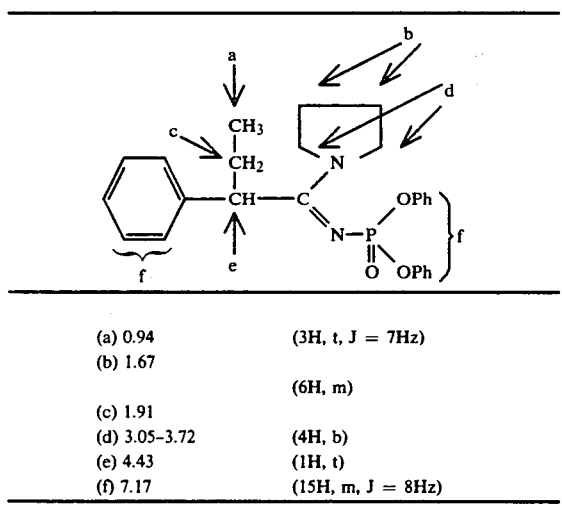

| (a) 0.94 | (3H, t, J = 7Hz) |
| (b) 1.67 | |
| | (6H, m) |
| (c) 1.91 | |
| (d) 3.05–3.72 | (4H, b) |
| (e) 4.43 | (1H, t) |
| (f) 7.17 | (15H, m, J = 8Hz) |

EXAMPLE 26

The process was similar to that as described in Example 25 except that the reaction was carried out under argon atmosphere to obtain 1.84 g of the desired amidine (yield: 82%). The product had physical properties as described in Example 25.

EXAMPLE 27

Preparation of diphenyl N-(2-phenyl-1-pyrrolidinobutylidene)phosphoramidate

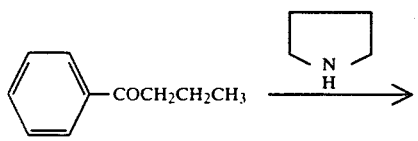

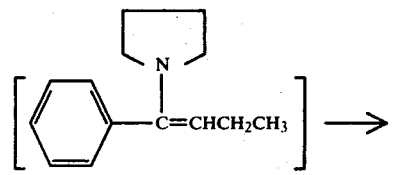

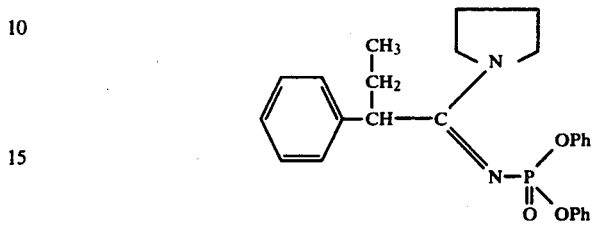

wherein Ph represents phenyl.

0.74 g of n-butyrophenone, 1.07 g of pyrrolidine and 0.07 g of boron trifluoride etherate were dissolved in 50 ml of benzene and subjected to the reaction as described in Example 2. The resulting reaction mixture was subjected to a distillation under a reduced pressure to remove the solvent and then under argon atmosphere 15 ml of tetrahydrofuran and 1.65 g of DPPA were added. The mixture was worked up as described in Example 25 to obtain 1.81 g of the desired amidine (yield from the raw material ketone: 81%). Physical properties of the product were same with those as described in Example 25.

EXAMPLE 28

Preparation of diphenyl N-(2-methyl-2-phenyl-1-pyrrolidinopropylidene) phosphoramidate

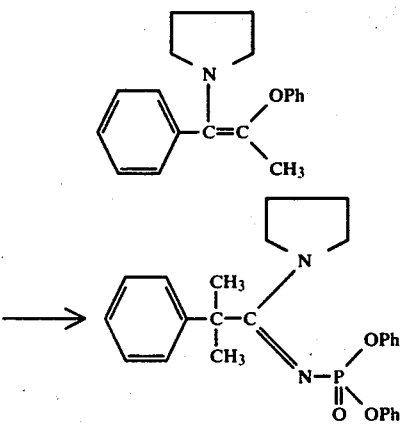

wherein Ph represents phenyl.

805 mg of enamine prepared by the process as described in J. Org. Chem. Vol. 32, page 213 (1976) and 1.32 g of DPPA were dissolved in 12 ml of tetrahydrofuran. The mixture was stirred under argon atmosphere for 1 hour at room temperature and 1 hour at 40° C. and then refluxed for 2 hours. The reaction mixture was subjected to the work up as described in Example 12 to obtain 1.25 g of the desired amidine (yield: 70%). The crude product was recrystallized from ethyl acetate-hexane to obtain colorless needles having melting point of 87° to 88.5° C.

Elemental Analysis: $C_{26}H_{29}NO_3P$ Cal. C: 69.63; H:6.52; N:6.25; Found C:69.56; H: 6.57; N:6.31.

NMR spectrum: δ ppm, $CCl_4$

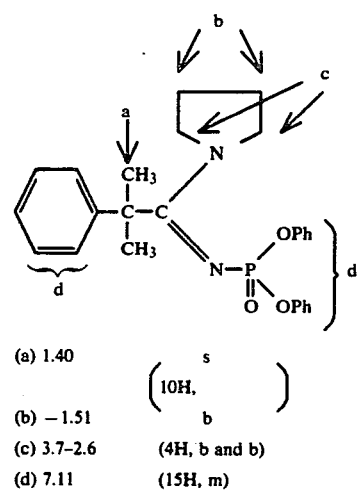

| | |
|---|---|
| (a) 1.40 | (10H, b) |
| (b) −1.51 | |
| (c) 3.7–2.6 | (4H, b and b) |
| (d) 7.11 | (15H, m) |

EXAMPLE 29

Preparation of diphenyl N-(2-phenyl-1-pyrrolidino-4-pentenylidene)phosphoramidate

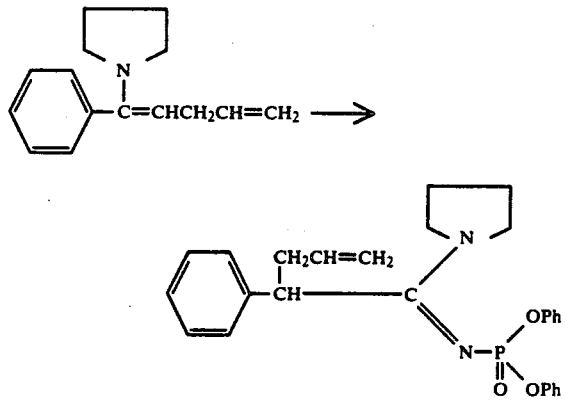

wherein Ph represents phenyl.

1.07 g of enamine prepared by the process as described in Example 3 and 1.65 g of DPPA were dissolved in 15 ml of tetrahydrofuran. The mixture was stirred under argon atmosphere for 1 hour at room temperature and 1 hour at 40° C. and then refluxed for 2 hours. The reaction mixture was subjected to the work up as described in Example 12 to obtain 1.84 g of the desired amidine (yield: 80%).

IR spectrum: $\nu_{max}^{cap}$ cm$^{-1}$ 1585, 1565, 1489, 1242, 1228, 1200 and 917

NMR spectrum: δ ppm, $CCl_4$

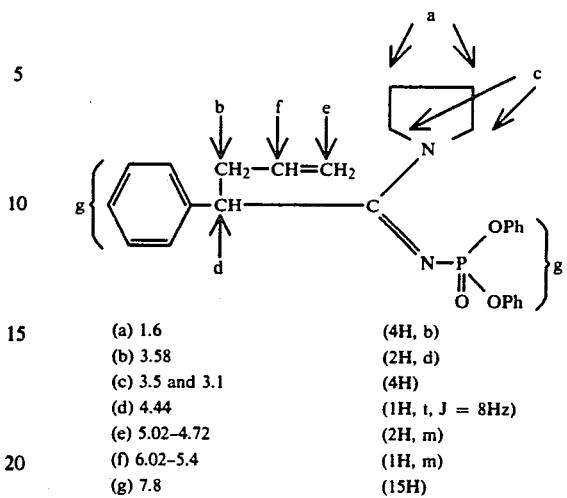

| | |
|---|---|
| (a) 1.6 | (4H, b) |
| (b) 3.58 | (2H, d) |
| (c) 3.5 and 3.1 | (4H) |
| (d) 4.44 | (1H, t, J = 8Hz) |
| (e) 5.02–4.72 | (2H, m) |
| (f) 6.02–5.4 | (1H, m) |
| (g) 7.8 | (15H) |

EXAMPLE 30

Preparation of diphenyl N-(2-phenyl-1-pyrrolidinoethylidene)phosphoramidate

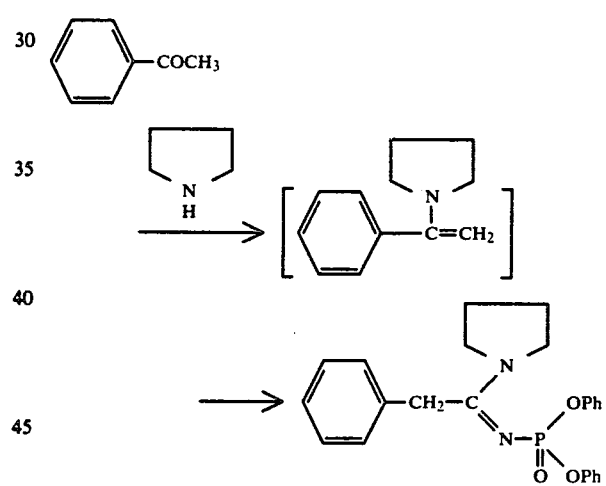

wherein Ph represents phenyl.

0.60 g of acetophenone, 1.17 g of pyrrolidine and 0.07 g of boron trifluoride etherate were dissolved in 30 ml of toluene and refluxed under argon atmosphere for 18 hours using a Cope water separator and molecular sieve 4A as the dehydrating agent. The reaction mixture was subjected to a distillation under a reduced pressure to remove the solvent and then 15 ml of tetrahydrofuran and 1.65 g of DPPA was added. The resulting mixture was allowed to react under argon atmosphere by stirring same for 24 hours at room temperature and then subjected to the work up as described in Example 12 to obtain 101 mg of the desired amidine (yield from the starting acetophenone: 5%).

IR spectrum: $\nu_{max}^{cap}$ cm$^{-1}$ 1567, 1486, 1246, 1220, 1198 and 920

NMR spectrum: δ ppm, $CCl_4$

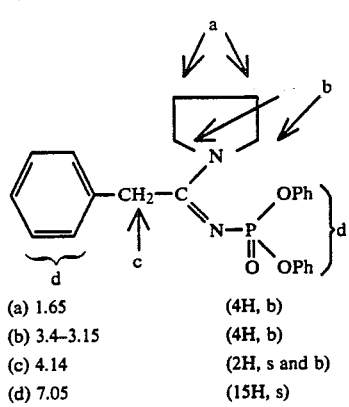

| | |
|---|---|
| (a) 1.65 | (4H, b) |
| (b) 3.4–3.15 | (4H, b) |
| (c) 4.14 | (2H, s and b) |
| (d) 7.05 | (15H, s) |

EXAMPLE 31

Preparation of diphenyl N-[2-(4-methoxyphenyl)-1-pyrrolidinoethylidene]phosphoramidate

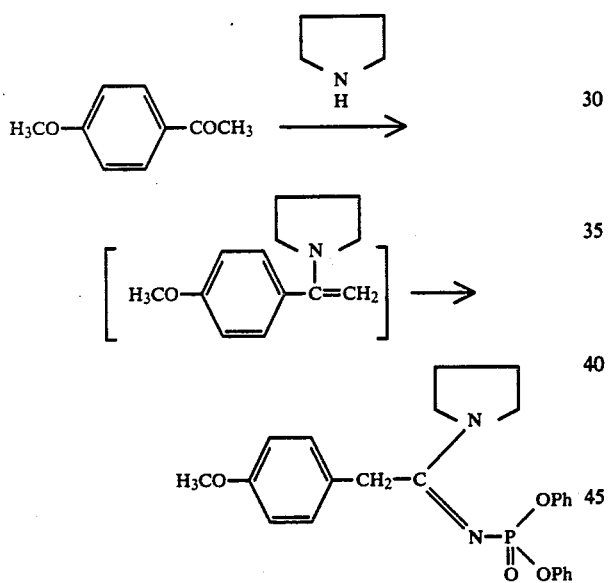

wherein Ph represents phenyl.

0.751 g of 4-methoxyacetophenone, 1.07 g of pyrrolidine and 0.03 g of boron trifluoride etherate were dissolved in 30 ml of toluene and subjected to the reaction as described in Example 30. The reaction mixture was subjected to a distillation under a reduced pressure to remove the solvent, 1.65 g of DPPA and 15 ml of tetrahydrofuran were added and then subjected to the reaction as well as work up as described in Example 30 to obtain 245 mg of the desired amidine (yield from methoxyacetophenone: 11%).

Melting point: 72° to 75.5° C.
IR spectrum: $\nu_{max}^{KBr}$ cm$^{-1}$
1562, 1484, 1239, 1196 and 917
NMR spectrum: δ ppm, CDCl$_3$

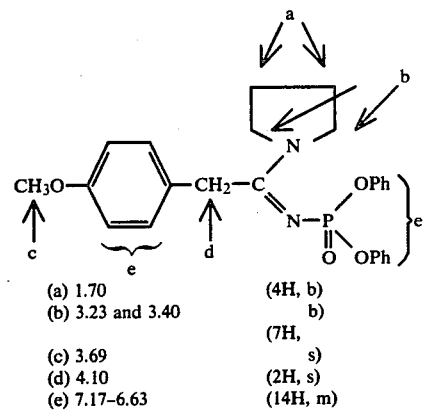

| | |
|---|---|
| (a) 1.70 | (4H, b) |
| (b) 3.23 and 3.40 | b) |
| (c) 3.69 | (7H, s) |
| (d) 4.10 | (2H, s) |
| (e) 7.17–6.63 | (14H, m) |

EXAMPLE 32

Preparation of 2-phenylpropionic acid

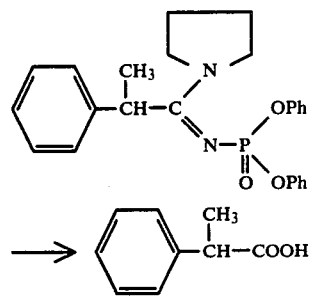

wherein Ph represents phenyl.

1.303 g of amidine prepared by the process as described in Example 12, 13 or 14 and 2.94 g of potassium hydroxide were dissolved in 40 ml of ethylene glycol and refluxed for 12 hours. The reaction mixture was diluted with 300 ml of water and pH of the solution was made about 9 by passing therein carbon dioxide gas and then washed with ethyl ether. After having acidified with hydrochloric acid, the aqueous phase was extracted with ethyl acetate and then an organic phase was washed by water and saturated sodium chloride solution, dried on magnesium bisulfate and distilled under a reduced pressure to remove the solvent and to obtain 408 g of the desired acid (yield 91%).

Boiling point: 103° to 105° C./3 mmHg

EXAMPLE 33

Preparation of 2-(4-isobutylphenyl)propionic acid

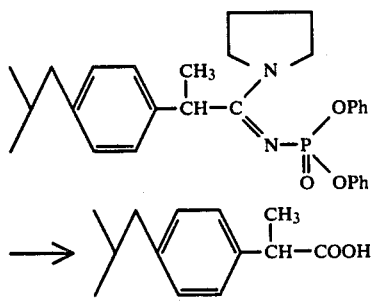

wherein Ph represents phenyl.

1.473 g of amidine prepared by the process as described in Example 17, 18 or 19 and 2.95 g of potassium hydroxide were dissolved in 35 ml of ethylene glycol and refluxed for 12 hours and then subjected to the work up as described in Example 32 to obtain 489 mg of the desired acid (yield: 79%). The crude product was recrystallized from petroleum benzene to obtain colorless needles having melting point of 74° to 75° C.

EXAMPLE 34

Preparation of 2-(6-methoxy-2-naphthyl)propionic acid

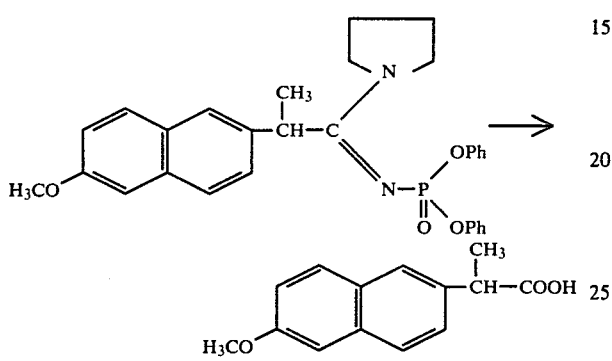

wherein Ph represents phenyl.

515 mg of amidine prepared by the process as described in Example 20 or 21 and 0.35 g of potassium hydroxide were dissolved in 10 ml of ethylene glycol and refluxed for 8 hours. The reaction mixture was subjected to the work up as described in Example 32 to obtain the desired acid (yield: 83%).

The crude product was purified by a silica-gel chromatography with chloroform–methanol–acetic acid (200:10:1) to obtain 157 mg of colorless needle crystals (yield: 71%).

Melting point: 151.5°–152.5° C.

EXAMPLE 35

Preparation of 2-(2-dibenzofuranyl)propionic acid

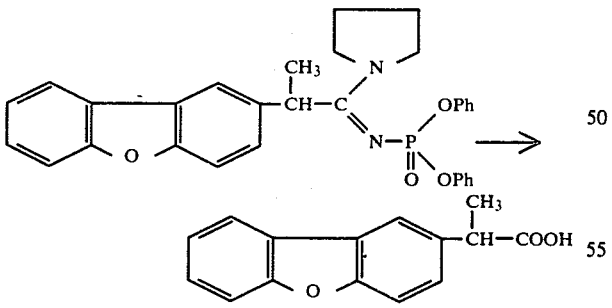

wherein Ph represents phenyl.

825 mg of amidine prepared by the process as described in Example 22 and 1.57 g of potassium hydroxide were dissolved in 30 ml of ethylene glycol and refluxed for 7 hours. The reaction mixture was subjected to the work up as described in Example 32 to obtain 345 mg of the desired acid (yield: 92%). The crude product was recrystallized from ethyl acetate-hexane to obtain colorless needles having melting point of 141° to 142.5° C.

EXAMPLE 36

Preparation of 2-(2-fluoro-4-biphenyl)propionic acid

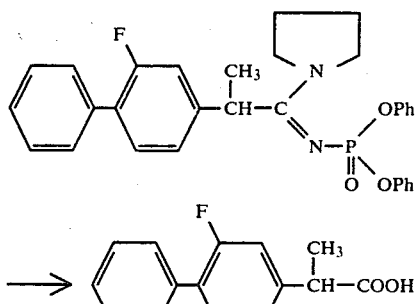

wherein Ph represents phenyl.

528 mg of amidine prepared by the process as described in Example 24 and 0.3 g of potassium hydroxide were dissolved in 10 ml of ethylene glycol and refluxed for 8 hours. The reaction mixture was subjected to the work up as described in Example 32 to obtain 73 mg of the desired acid (yield: 30%). The crude product was recrystallized from ethyl acetate-hexane to obtain colorless crystals having melting point of 113° to 114° C.

EXAMPLE 37

Preparation of 2-phenylbutyric acid

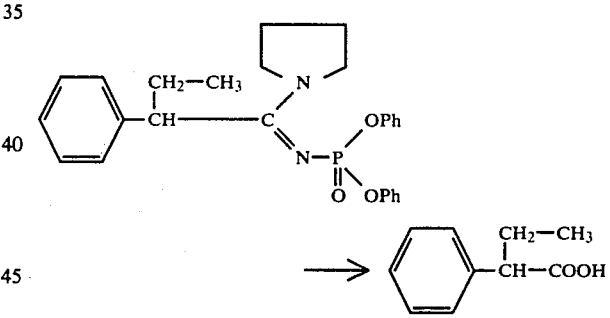

wherein Ph represents phenyl.

0.45 g of amidine prepared by the process as described in Example 25, 26 or 27 and 1.00 g of potassium hydroxide were dissolved in 20 ml of ethylene glycol and refluxed for 6 hours. The reaction mixture was poured into 200 ml of water and then to the resulting solution, carbon dioxide gas was bubbled to make pH to about 9. After having been washed 5 times with 50 ml of ethyl ether, the aqueous phase was acidified with conc. hydrochloric acid and extracted 4 times with 50 ml of ethyl acetate. The extracts were subsequently washed with water and saturated sodium chloride solution and then dried on magnesium sulfate. The residue obtained by distilled out the solvent under a reduced pressure was purified by chromatography to obtain 0.15 g of the desired acid (yield: 91%) having melting point of 42° to 43° C.

EXAMPLE 38

Preparation of 2-methyl-2-phenylpropionic acid

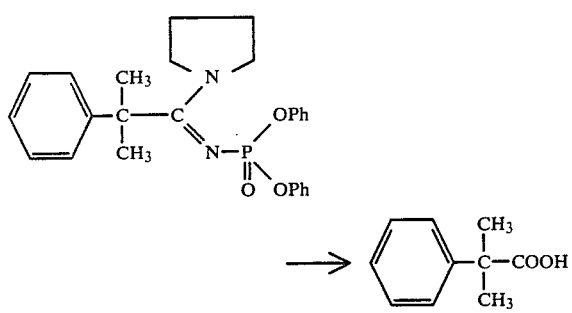

wherein Ph represents phenyl.

0.45 g of amidine prepared by the process as described in Example 28 and 1.00 g of potassium hydroxide were dissolved in 20 ml of ethylene glycol and refluxed for 6 hours. The reaction mixture was subjected to the work up as described in Example 37 to obtain 0.165 g of the desired acid having melting point of 75° to 77.5° C.

EXAMPLE 39

Preparation of 2-allylphenylacetic acid

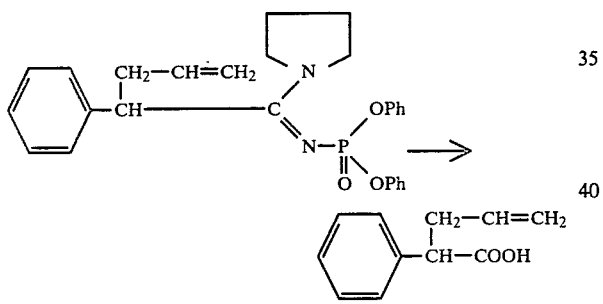

wherein Ph represents phenyl.

0.46 g of amidine prepared by the process as described in Example 29 and 1.00 g of potassium hydroxide were dissolved in 20 ml of ethylene glycol and refluxed for 6 hours. The reaction mixture was subjected to the work up as described in Example 37 to obtain 0.16 g of the desired acid (yield: 91%) having melting point of 34° C.

EXAMPLE 40

Preparation of 2-(3-benzoylphenyl)propionic acid

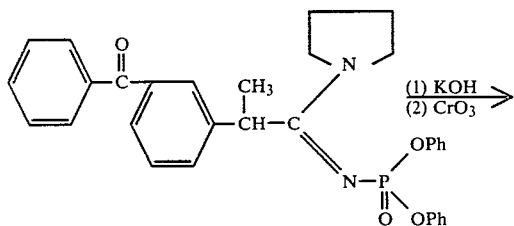

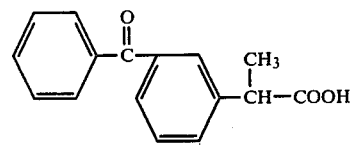

wherein Ph represents phenyl.

423 mg of amidine prepared by the process as described in Example 23 and 0.77 g of potassium hydroxide were dissolved in 15 ml of ethylene glycol and refluxed for 6 hours.

The reaction mixture was subjected to the work up as described in Example 37 to obtain 139 mg of the crude acid.

To the crude acid dissolved in 5.5 ml of acetone, Jones reagent (E. R. H. Jones J. Chem. Soc. 1953, 2548) was added until a blue-yellow solution turns to a red-yellow and then a small amount of isopropanol was added to turn the the solution color to colorless. The resulting acid solution was dissolved in 190 ml of chloroform, washed with water, dried on magnesium sulfate and distilled under a reduced pressure to remove the soluvent and obtain 123 mg of the desired acid as colorless viscous oil (yield: 62%).

IR spectrum: $\nu_{max}^{cap}$ cm$^{-1}$
1730, 1705 (-COOH), 1655

NMR spectrum: δ ppm, CDCl$_3$

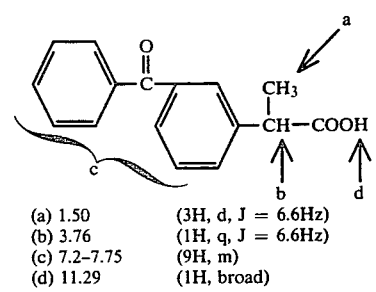

| | |
|---|---|
| (a) 1.50 | (3H, d, J = 6.6Hz) |
| (b) 3.76 | (1H, q, J = 6.6Hz) |
| (c) 7.2–7.75 | (9H, m) |
| (d) 11.29 | (1H, broad) |

What is claimed is:
1. An amidine compound represented by the formula

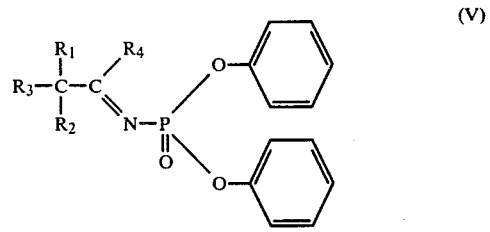

(V)

wherein R$_1$ represents hydrogen or lower alkyl, R$_2$ represents hydrogen, lower alkyl or allyl, R$_2$ represents phenyl, lower alkyl substituted phenyl, lower alkoxy substituted phenyl, cyclohexenyl substituted phenyl, benzoyl substituted phenyl, methoxy substituted naphthyl, dibenzofuranyl, or halogen substituted biphenyl and R$_4$ represents 1-piperidyl.

* * * * *